United States Patent [19]
Moumane et al.

[11] Patent Number: 5,957,965
[45] Date of Patent: Sep. 28, 1999

[54] SACRAL MEDICAL ELECTRICAL LEAD

[75] Inventors: Farid Moumane, Trelon; Jean Robinet, Anor; Benoit Deruyver, Avesnes-sur-Helpe, all of France; Ronald Lee Mezera, Burnsville, Minn.; Robert Mark Pearson, Woodbury, Minn.; John Anthony Fontecchio, Plymouth, Minn.

[73] Assignee: Medtronic, Inc., Minneapolis, Minn.

[21] Appl. No.: 08/811,054

[22] Filed: Mar. 3, 1997

[51] Int. Cl.⁶ .................................................. A61N 1/05
[52] U.S. Cl. ............................................................ 607/117
[58] Field of Search .............................. 607/117, 40, 41, 607/126, 130, 149, 122, 116

[56] References Cited

U.S. PATENT DOCUMENTS

| | | |
|---|---|---|
| 4,341,221 | 7/1982 | Testerman . |
| 4,602,624 | 7/1986 | Naples et al. . |
| 4,607,639 | 8/1986 | Tanagho et al. . |
| 4,940,065 | 7/1990 | Tanagho et al. . |
| 5,344,438 | 9/1994 | Testerman et al. ...................... 607/118 |
| 5,484,445 | 1/1996 | Knuth ...................... 606/129 |
| 5,733,322 | 3/1998 | Starkebaum ........................... 607/117 |

*Primary Examiner*—Scott M. Getzow
*Attorney, Agent, or Firm*—Michael J. Jaro; Harold R. Patton

[57] ABSTRACT

A sacral medical electrical lead which may be implanted and reliably fixed for a temporary period of time within the sacrum in a minimally invasive manner. The lead features a lead body having a electrical conductor positioned within an insulator sheath, a connector for electrically coupling the electrical conductor to a pulse generator, an electrode located on a distal end of the lead body, the electrode electrically coupled to the conductor, and an anchor for anchoring the lead body to sacral tissue, the anchor integral with the insulator sheath. In the preferred embodiment the anchor comprises a notched section in which the insulation of the lead body presents a macroscopically roughened surface which can thereby engage into the tissue without causing damage to the tissue.

10 Claims, 4 Drawing Sheets

SACRAL MEDICAL ELECTRICAL LEAD

FIELD OF THE INVENTION

This invention relates to an anchoring system and specifically to a sacral medical electrical lead which may be implanted and reliably fixed for a temporary period of time within the sacrum in a minimally invasive manner.

BACKGROUND OF THE INVENTION

The present invention relates to the art of selective nerve stimulation. The invention finds particular application in conjunction with urination control and will be described with particular reference thereto. It is to be appreciated that the invention is also applicable to control other aspects of the nervous system, such as for fecal incontinence, penile erection, and others.

The organs involved in bladder, bowel, and sexual function receive much of their control via the second, third, and fourth sacral nerves, commonly referred to as S2, S3 and S4 respectively. Electrical stimulation of these various nerves has been found to offer SOME control over these functions. Several techniques of electrical stimulation may be used, including stimulation of nerve bundles within the sacrum.

The sacrum, generally speaking, is a large, triangular bone situated at the lower part of the vertebral column, and at the upper and back part of the pelvic cavity. The spinal canal runs throughout the greater part of this bone. It lodges the sacral nerves, and is perforated by the anterior and posterior sacral foramina through which these pass out.

Several systems of stimulating sacral nerves exist. For example, U.S. Pat. No. 4,607,639 to Tanagho et al. entitled "Method and System for Controlling Bladder Evacuation", incorporated herein by reference, and the related U.S. Pat. No. 4,739,764 to Lue et al. entitled "Method for Stimulating Pelvic Floor Muscles for Regulating Pelvic Viscera", also incorporated herein by reference, disclose implanting an electrode on at least one nerve controlling the bladder. In one embodiment the electrode is percutaneously implanted through the dorsum and the sacral foramen of the sacral segment S3 for purposes of selectively stimulating the S3 sacral nerve. The electrode is positioned using a hollow spinal needle through a foramen (a singular foramina) in the sacrum. The electrode is secured by suturing the lead body in place. U.S. Pat. No. 4,569,351 to Tang entitled "Apparatus and Method for Stimulating Micturition and Certain Muscles in Paraplegic Mammals", incorporated herein by reference, discloses use of electrodes positioned within the sacrum to control bladder function.

Typically electrical stimulation of the nerves within the sacrum is accomplished by positioning a lead having at least one electrode at its distal end through a foramen of the sacrum and proximate the nerve. Not all patients, however, are suitable for such stimulation. In fact, at present there is not a reliable screening tool to identify patients who would or would not benefit from sacral nerve stimulation other than to actually stimulate such nerves.

Placing a lead into the sacrum in order to assess the efficacy of sacral nerve stimulation may be performed percutaneously, that is, simply using a needle. Leads implanted in such a manner, however, have to date been difficult to reliably anchor in position. Techniques such as taping the exterior lead body to the patient are not wholly satisfactory. Other techniques which are effective to anchor a sacral lead, such as screwing the lead to the sacral bone, are much too invasive for a screening procedure. Thus there exits a need for a medical electrical lead which may be safely and effectively implanted into the sacrum and anchored within in a minimally invasive manner.

SUMMARY OF THE INVENTION

A sacral medical electrical lead which may be implanted and reliably fixed for a temporary period of time within the sacrum in a minimally invasive manner. In the preferred embodiment the lead features a lead body having a electrical conductor positioned with an insulator sheath, a connector for electrically coupling the electrical conductor to a pulse generator, an electrode located on a distal end of the lead body, the electrode electrically coupled to the conductor, and means for anchoring the lead body to sacral tissue, the anchoring means integral with the insulator sheath. In the preferred embodiment the anchoring means comprises a notched section in which the insulation of the lead body presents a macroscopically roughened surface which can thereby engage into tissue without causing damage to the tissue.

The FIGS. are not necessarily to scale.

DETAILED DESCRIPTION OF THE PREFERRED EMBODIMENTS

Figure 1:
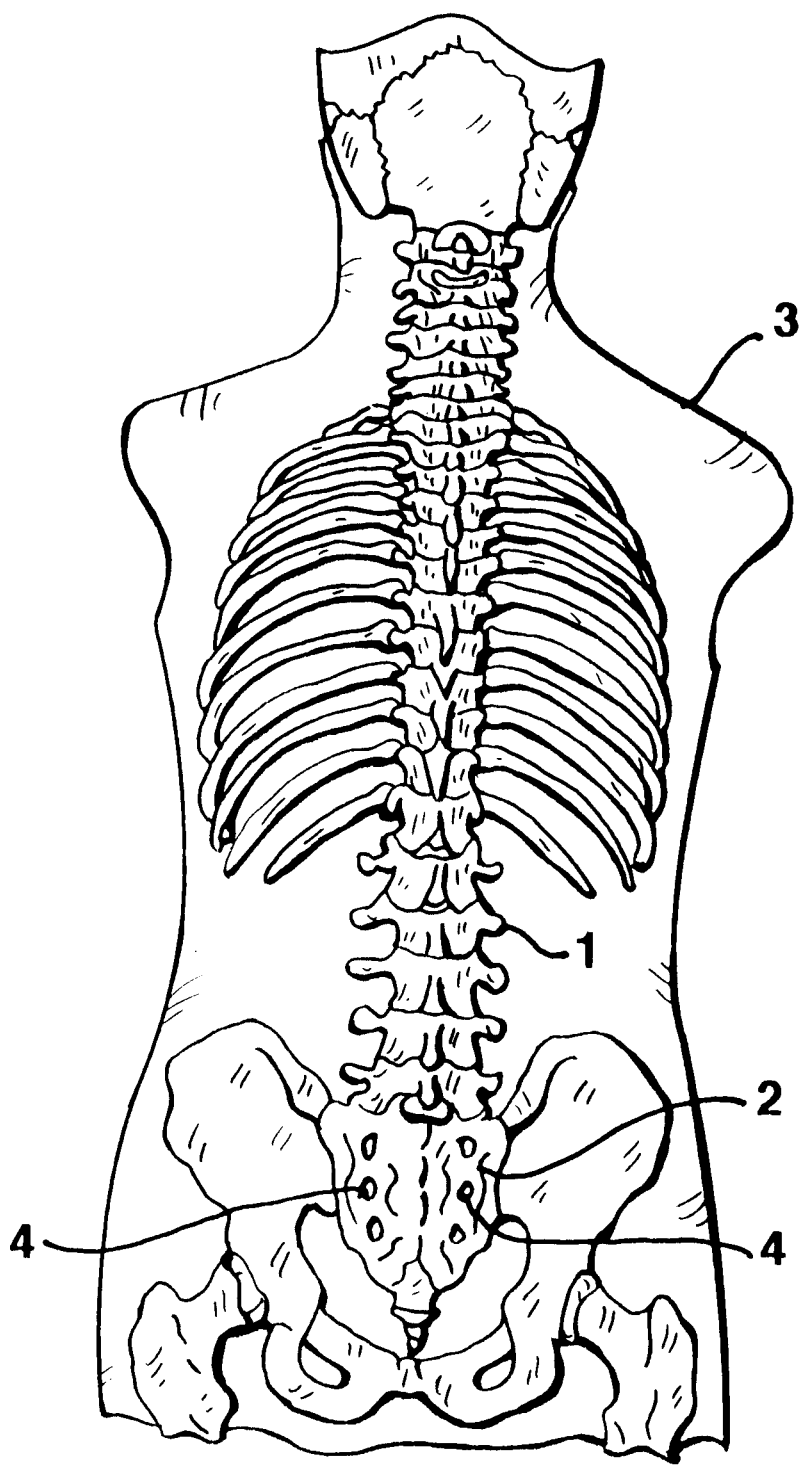
FIG. 1 is a posterior view of the spinal column showing the location of the sacrum relative to an outline of a body.

FIG. 1 is a posterior view of the spinal column 1 showing the location of the sacrum 2 relative to an outline of a body 3. As seen, the sacrum 2 has a series of holes, known as foramina 4, therethrough. Each foramen 4 (as they are referred to in the singular) provides access to the sacral ventral nerves (not shown). As discussed above electrical stimulation of these nerves is useful to effect control of an organ, such as a bladder (not shown).

Figure 2A:
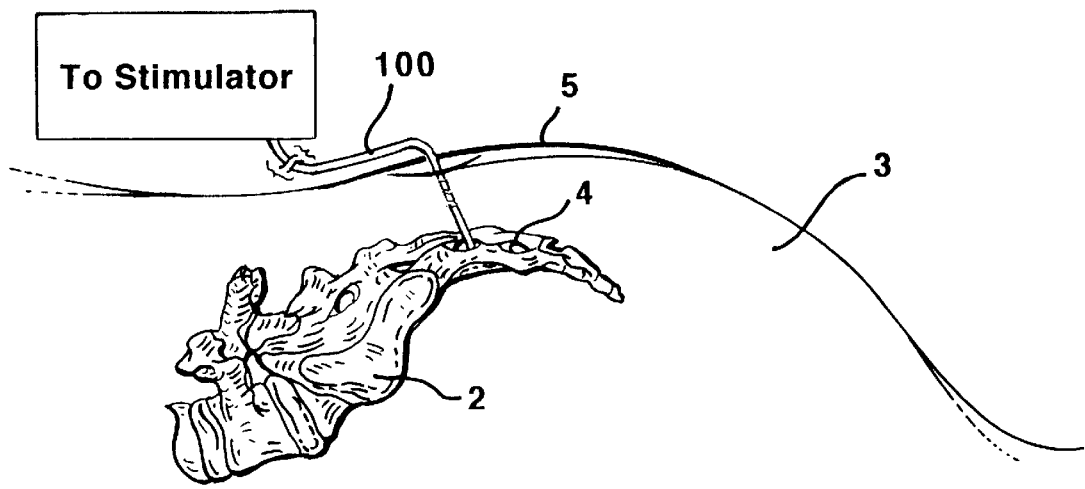
FIG. 2A is a side view of the sacrum having a lead implanted.

FIG. 2A is a side view of the sacrum having a lead implanted. As seen, the sacrum 2 has a series of foramina 4 located near the dorsal surface 5 and a patient 3. Lead 100 may be inserted using a percutaneous procedure into the foramina so that the electrode at the distal end is positioned near the sacral nerve.

Figure 2B:
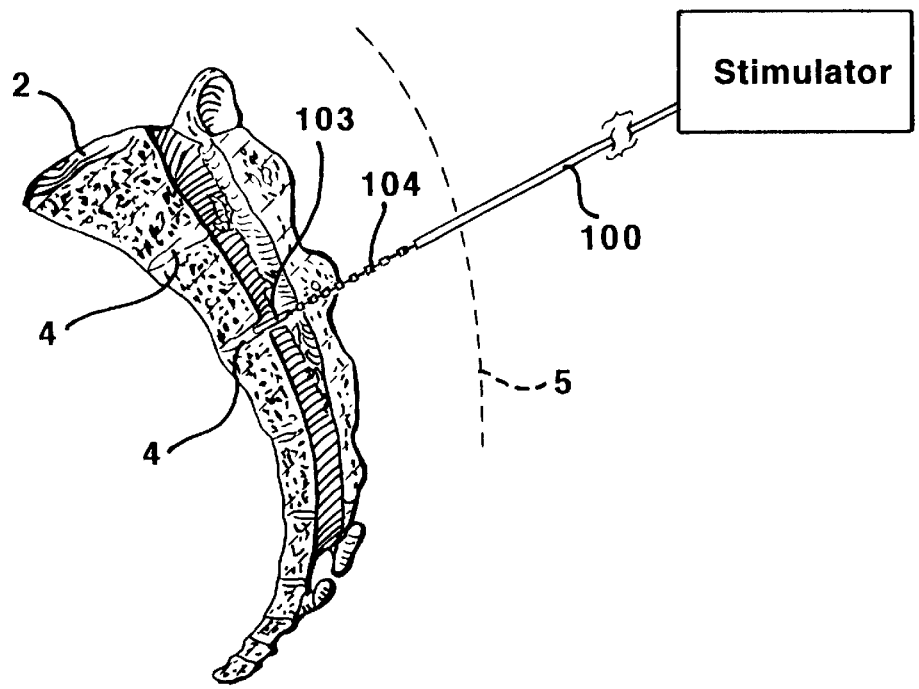
FIG. 2B is a sectional view of the sacrum showing a stimulation system which features a medical electrical lead of the preset invention placed within the sacrum.

FIG. 2B is the side sectional view of a lead 100 implanted into the sacrums. As seen, the lead has an electrode 103 at its distal end. Positioned remote from the electrode along the lead body is anchoring portion 104. Through this configuration the electrode may be positioned adjacent the sacral nerve while the anchoring portion is remote from the sacral nerve. This permits the electrode to be reliably anchored next to the nerve without causing damage to the nerves.

For example, electrode 1b could be percutaneously placed on the S3 sacral nerve with the external extremity of the wire attached to the electrode then being taped to the skin, along with a receiver connected thereto. The patient could then resume his day-to-day lifestyle and be allowed to stimulate the nerve or nerves artificially via the receiver (not shown). If the response is positive and complete relief is achieved, the electrode or electrodes could be permanently implanted or temporarily implanted for the purpose of correcting any dysfunction by "retraining" the nerve and associated muscles. Should little or no improvement result, the same procedure could be followed to accurately ascertain which nerve or nerves require stimulation. Thus, this invention contemplates not only the implantation of one or more electrodes in the sacral nervous system for controlling evacuation of a visceral organ or the like, but also contemplates use of such electrodes and procedures to rehabilitate muscle dysfunction by neuromodulation of muscular behavior.

Figure 3:
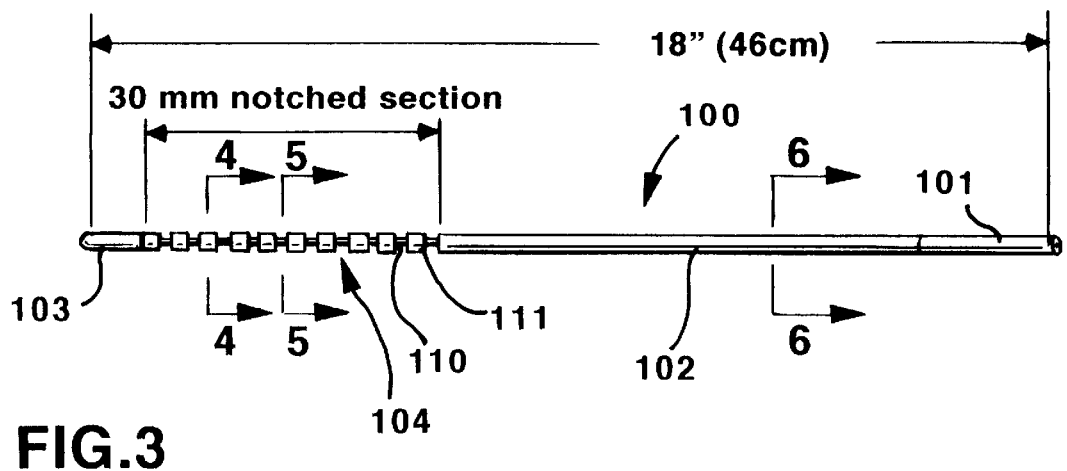
FIG. 3 is a side view of a medical electrical lead of the present invention.

FIG. 3 is a side view of an medical electrical lead of the present invention. As seen lead 100 has essentially three sections, connector pin 101, lead body 102, and electrode 103. Connector pin is preferably a stainless steel platinum iridium alloy. Likewise, electrode is preferably a stainless steel platinum iridium alloy. Lead body is preferably constructed with a bundle stranded conductor of stainless steel covered by a sheath of PTFE. Of course other materials may also be selected for either the conductor or sheath. As seen, located at the distal end of lead body is anchoring portion 104. Anchoring portion preferably comprises a presents a macroscopically roughened surface which can thereby engage into the sacral tissue without causing damage to the sacral tissue. In the preferred embodiment anchoring portion consists of a series of smaller diameter sections, called notches 110 positioned in between a series of larger diameter sections called ridges 111. As discussed above these sections permit anchoring portion of lead body to engage within the tissue above the sacrum so as to permit the lead to be reliably positioned without invasive procedure or damaging tissue. In particular, the ridges are able to engage in a non destructive manner with the tissue so as to permit the electrode to be reliably anchored within the sacrum near a nerve.

In the preferred embodiment lead body has a total length 458 +/−6 mm Electrode is preferably 6 mm in length. Anchoring portion is between 20 and 40 mm long with 30 mm preferred. Electrode preferably has a diameter of 0.6 mm as compared to the lead body which preferably has a diameter of 0.7 mm. Notches preferably have a diameter of 0.8 mm, each notch and ridge are preferably 1.5 mm in length. Lead body is most flexible along anchoring portion.

Figure 4:
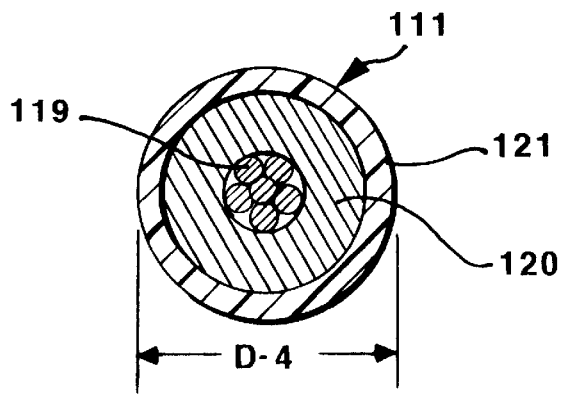
FIG. 4 is a sectional view of the lead of FIG. 3 across a ridge.

FIG. 4 is a sectional view of the lead of FIG. 3 across a ridge 111. As seen ridge is formed by covering conductor 119 with a layer of inner insulation 120 and with a layer of outer insulation 121. Inner insulation is preferably PTFE and outer insulation is preferably parylene. Outer insulation is preferably at least 0.0051 mm (0.0002 inches) in thickness. As seen ridge has an outer diameter D-4.

Figure 5:
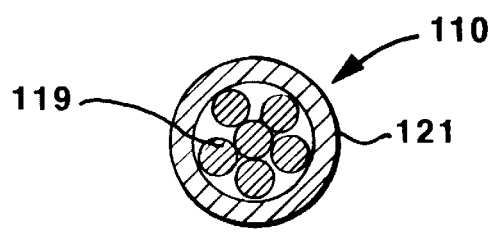
FIG. 5 is a sectional view of the lead of FIG. 3 across a furrow.

FIG. 5 is a sectional view of the lead of FIG. 3 across a notch. As seen furrow is formed by the absence of the inner insulation 120 but still with the presence of the outer insulation 121. In the preferred embodiment the NOTCHES and notches are manufactured through first covering the conductor with the inner insulation and then removing portions of the inner insulation in the area of the anchoring portion all the way down to the conductor is exposed. Next anchoring portion is covered with a coating of the outer insulation such that the formerly exposed portions of the conductor are covered and the entire length of the lead body is electrically insulated.

Figure 6:
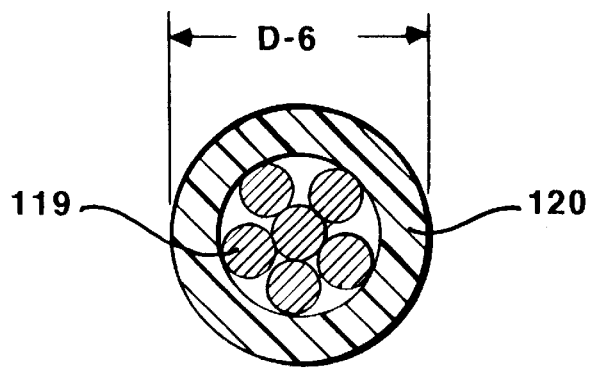
FIG. 6 is a sectional view of the lead of FIG. 3 across a portion of lead body proximal to anchoring portion.

FIG. 6 is a sectional view of the lead of FIG. 3 across a portion of the lead body proximal to the anchoring portion. As seen Insulation 120 covers conductor 119. Lead body has an outer diameter D-6. As seen in a comparison with FIG. 4, outer diameter D-6 is substantially the same as the outer diameter of ridge, D-4. In the preferred embodiment lead body outer diameter is no greater than 0.635 mm (0.025 inches) anywhere along its length, including along anchoring portion.

Figure 7:
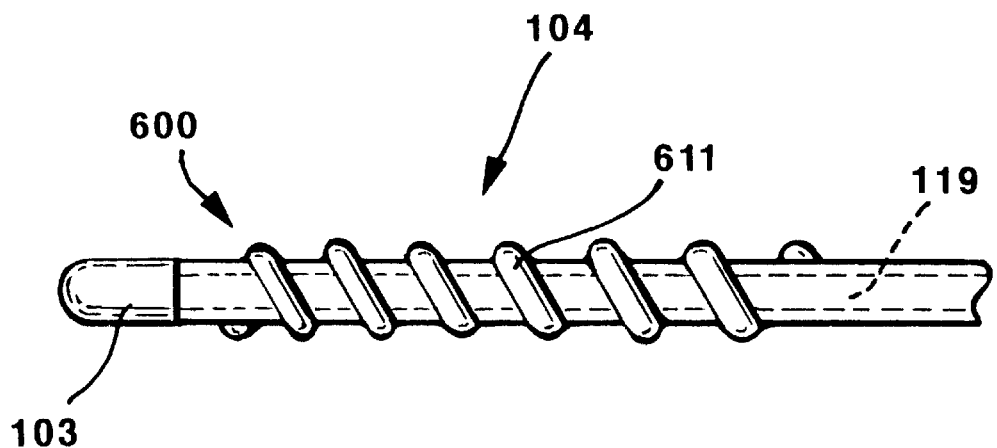
FIG. 7 is a view of an alternative lead.

Of course, other schemes may also be used to anchor the lead within the sacral tissue and still be within the scope of the present invention. Such schemes include providing lead body insulation as well as Geometries which have a higher friction as compared to conventional smooth outer surface lead bodies. An example of an alternative may be seen in FIG. 7. As seen, lead 600 features an electrode 103 at distal end coupled to conductor 119 as already discussed above. Anchoring portion 104 is constructed through a second piece 611 of insulative material wrapped about the exterior of the lead body insulative sheath. Through this construction a macroscopically roughened area along lead body remote from the electrode is created. As discussed above this permits the lead body to engage into tissue and thus anchor electrode near a nerve without damaging tissue or the nerve.

Figure 8:
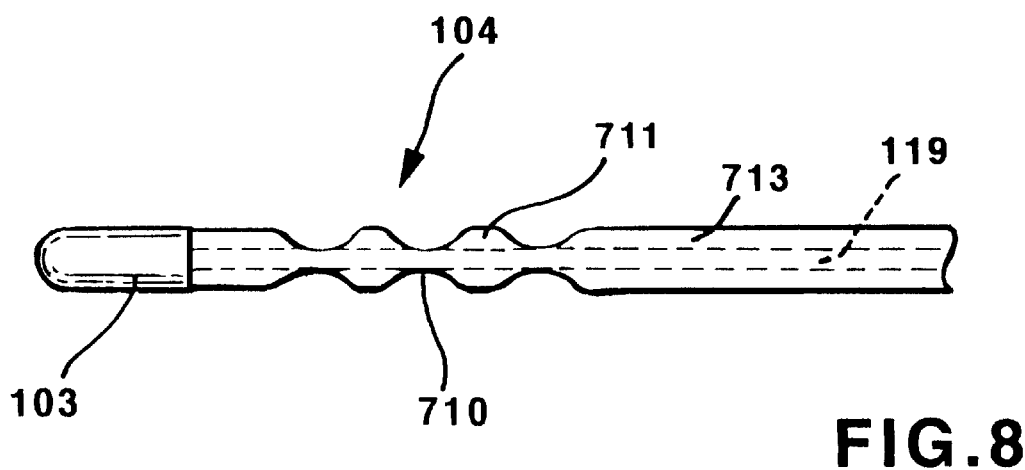
FIG. 8 is a view of an alternative lead.

A further alternate embodiment is seen in FIG. 8. As seen lead 700 features an electrode 103. As seen, lead 600 features an electrode 103 at distal end coupled to conductor 119 as already discussed above. Anchoring portion 104 is constructed through a series of indentations 710 pressed along the exterior of the lead body insulative sheath which form ridges 711. In the preferred embodiment ridges have the same outer diameter as does the smooth portion 713 of lead body. Through this construction a macroscopically roughened area along lead body remote from the electrode is created. As discussed above this permits the lead body to engage into tissue and thus anchor electrode near a nerve without damaging tissue or the nerve.

Although the invention has been described in detail with particular reference to a preferred embodiment and alternate embodiments thereof, it will be understood variations and modifications can be effected within the scope of the following claims. Such modifications may include substituting elements or components which perform substantially the same function in substantially the same way to achieve substantially the same result for those described herein.

What is claimed is:

1. A medical electrical stimulation system comprising:
   a medical electrical stimulator;
   a medical electrical lead coupled to the stimulator, the medical electrical lead having a lead body, the lead body having a electrical conductor positioned with a first insulator sheath and a second insulator sheath; means for electrically coupling the electrical conductor to a pulse generator, the means for electrical coupling located on a proximal end of tile lead body; an electrode located on a proximal end of the lead body, the electrode electrically coupled to the conductor, and means for anchoring the electrode within the sacrum, the anchoring means remote from the electrode wherein the electrode is within the sacrum, wherein the means for anchoring the electrode within the sacrum comprises a series of notches within the first insulator sheath, the notches extending into the first insulator sheath such that the electrical conductor is not covered by the first insulator sheath in the area of the notch and a second insulator sheath fixed to the first insulator sheath along the length of the series of notches, second insulator sheath fixed to the electrical conductor not covered by the first insulator sheath in the area of the notch.

2. A medical electrical stimulation system according to claim 1 wherein the anchoring means are located at a distance between 1.5 mm and 30.5 mm from the electrode, the anchoring means having a length of at least 29.5 mm.

3. A medical electrical stimulation system according to claim 1 the means for anchoring comprising a series of notches within the lead body.

4. A medical electrical lead comprising:

a lead body, the lead body having a electrical conductor positioned within an insulator sheath;

means for electrically coupling the electrical conductor to a pulse generator, the means for electrical coupling located on a proximal end of the lead body;

an electrode located on a proximal end of the lead body, the electrode electrically coupled to the conductor; and means for anchoring the electrode within the sacrum, the anchoring means integral with the insulator sheath wherein the means for anchoring the electrode within the sacrum comprises a series of notches within the first insulator sheath, the notches extending into the first insulator sheath such that the electrical conductor is not covered by tho first insulator sheath in the area of the notch.

5. A medical electrical lead according to claim 4 wherein the insulator sheath is a first insulator sheath fixed to the electrical conductor along the length of the electrical conductor.

6. A medical electrical lead according to claim 4 further comprising a second insulator sheath fixed to the first insulator sheath along the length of the series of notches, second insulator sheath fixed to the electrical conductor not covered by the first insulator sheath in the area of the notch.

7. A medical electrical lead according to claim 6 wherein the second insulator sheath is parylene.

8. A medical electrical lead according to claim 4 wherein the anchoring means are located at a distance between 1.5 mm and 30.5 mm from the electrode, the anchoring means having a length of at least 29.5 mm.

9. A medical electrical lead according to claim 4 wherein the means for anchoring comprising a series of notches within the lead body.

10. A medical electrical lead according to claim 4 wherein the anchoring means comprising a series of notches within the lead body, the lead body having a lead body outer diameter, the anchoring means having an anchoring means outer diameter, the anchoring means outer diameter no greater than the lead body outer diameter.

* * * * *